United States Patent
Augustine

[11] Patent Number: 5,928,274
[45] Date of Patent: *Jul. 27, 1999

[54] CONVECTIVE THERMAL BLANKET

[75] Inventor: Scott D. Augustine, Bloomington, Minn.

[73] Assignee: Augustine Medical, Inc., Eden Prairie, Minn.

[*] Notice: This patent is subject to a terminal disclaimer.

[21] Appl. No.: 08/904,566

[22] Filed: Aug. 4, 1997

Related U.S. Application Data

[63] Continuation of application No. 08/667,480, Jun. 24, 1996, Pat. No. 5,658,325, which is a continuation of application No. 08/380,264, Jan. 27, 1995, abandoned, which is a continuation of application No. 08/285,921, Aug. 3, 1994, abandoned, which is a continuation of application No. 08/063,214, May 18, 1993, Pat. No. 5,350,417.

[51] Int. Cl.$^6$ ......................................................... A61F 7/00
[52] U.S. Cl. ........................................... 607/107; 607/104
[58] Field of Search ................................... 607/104, 105, 607/107, 108; 604/113; 34/98, 99; 5/482, 413, 421, 423; 219/12; 441/38, 87, 40, 41, 90

[56] References Cited

U.S. PATENT DOCUMENTS

| | | | |
|---|---|---|---|
| 3,831,206 | 8/1974 | Geary | 5/413 |
| 4,572,188 | 2/1986 | Augustine et al. | 607/104 |
| 4,753,241 | 6/1988 | Brannigan et al. | 607/112 |
| 4,867,230 | 9/1989 | Voss | 607/108 |
| 5,106,373 | 4/1992 | Augustine et al. | 607/104 |
| 5,125,238 | 6/1992 | Ragan et al. | 5/423 |
| 5,165,400 | 11/1992 | Berke | 5/482 |
| 5,184,612 | 2/1993 | Augustine | 607/104 |
| 5,265,599 | 11/1993 | Stephenson et al. | 607/104 |
| 5,300,101 | 4/1994 | Augustine et al. . | |
| 5,300,102 | 4/1994 | Augustine et al. . | |
| 5,324,320 | 6/1994 | Augustine et al. . | |
| 5,336,250 | 8/1994 | Augustine . | |
| 5,343,579 | 9/1994 | Dickerhoff et al. . | |
| 5,350,417 | 9/1994 | Augustine | 607/104 |
| 5,360,439 | 11/1994 | Dickerhoff et al. | 607/104 |
| 5,405,370 | 4/1995 | Irani | 607/104 |
| 5,405,371 | 4/1995 | Augustine et al. . | |
| 5,443,488 | 8/1995 | Namenye et al. . | |

FOREIGN PATENT DOCUMENTS

| | | | |
|---|---|---|---|
| 311336 | 4/1989 | European Pat. Off. | 607/104 |

OTHER PUBLICATIONS

"Skin Surface Warming: Heat Flux and Central Temperature", in Anesthesiology, by D.I. Sessler, M.D., et al., vol. 73, pp. 218–224, 1990.

"Intraoperative Warming Therapies: A Comparison of Three Devices", by J.M. Hynson, M.D., et al., Journal of Clinical Anesthesiology, vol. 4, pp. 194–199, 1992.

*Primary Examiner*—Lee Cohen
*Attorney, Agent, or Firm*—Gray Cary Ware Freidenrich

[57] ABSTRACT

A convective thermal blanket is provided which warms or cools a patient's head and body areas by convection. The blanket includes a covering which has top and bottom layers of material, the covering being sealed along its periphery so as to form a plenum chamber. The head end of the covering has a recess for receiving a patient's head. The recess forms the head end of the covering into a pair of flaps, each flap being adapted to extend along a respective side of the patient's head and the covering below the recess being adapted to cover the patient's chest or body area. The recess also forms the plenum chamber into a main plenum chamber for the chest area and a pair of secondary plenum chambers, each secondary plenum chamber being in a respective flap for the head area. The covering has an inlet opening for receiving a gaseous medium for inflating the main plenum chamber and the secondary plenum chambers. The bottom layer of the covering has a plurality of apertures, which open into the main plenum chamber and the secondary plenum chambers, for discharging the gaseous medium over the patient's chest and head areas when the plenum chambers are inflated.

17 Claims, 6 Drawing Sheets

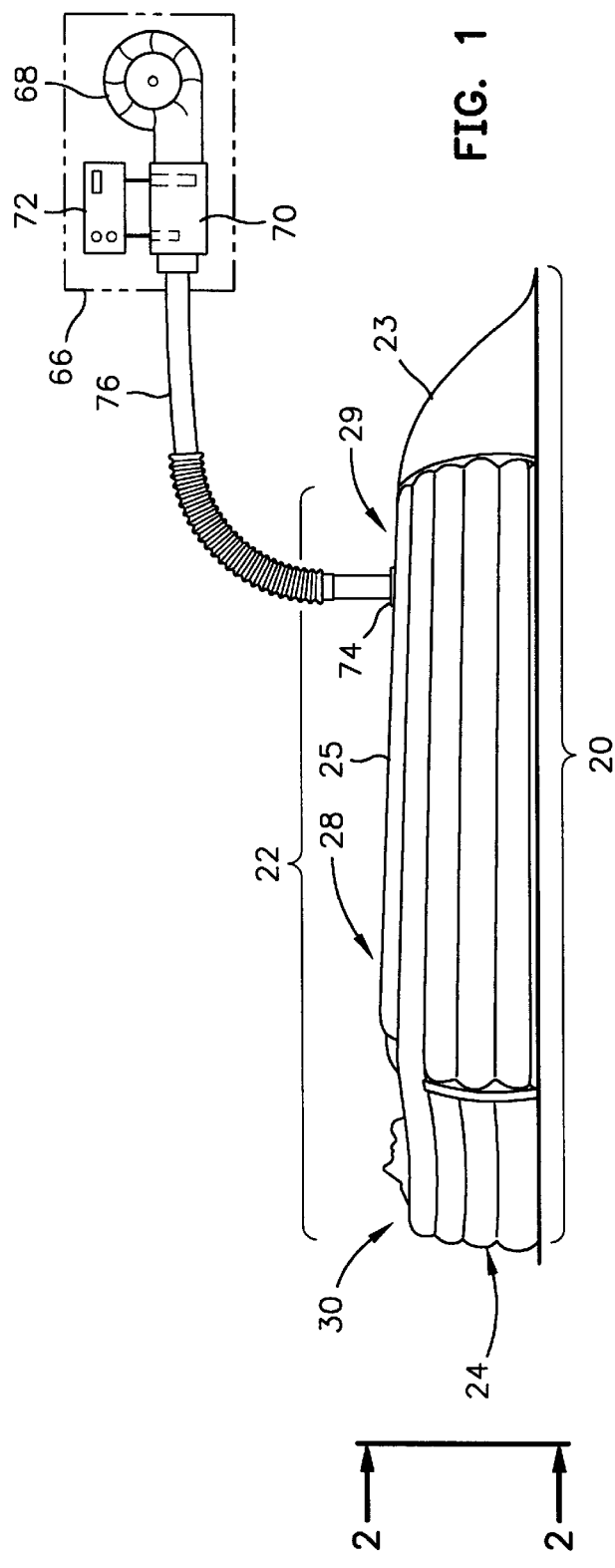
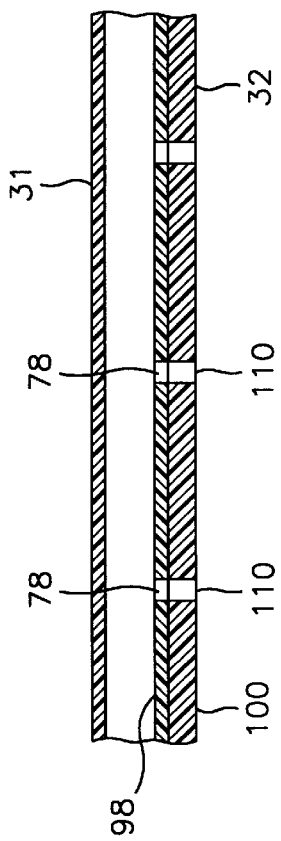
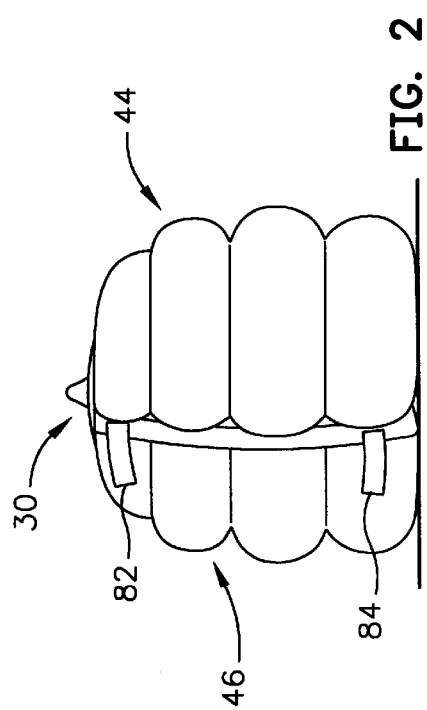

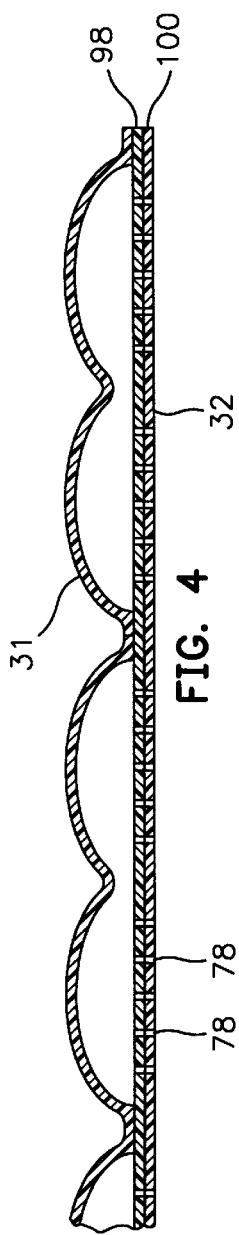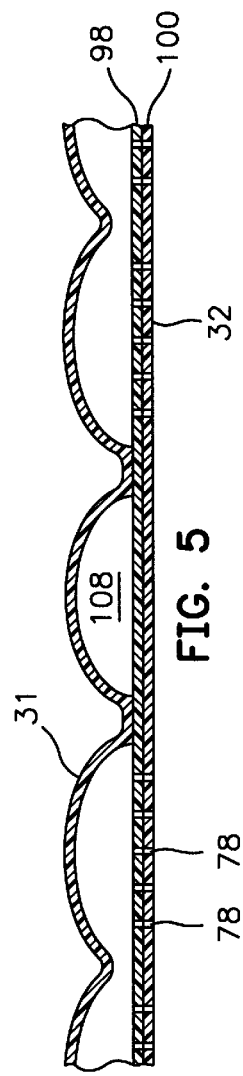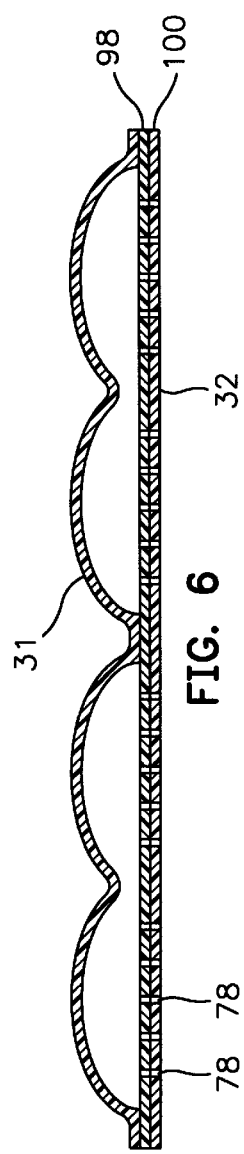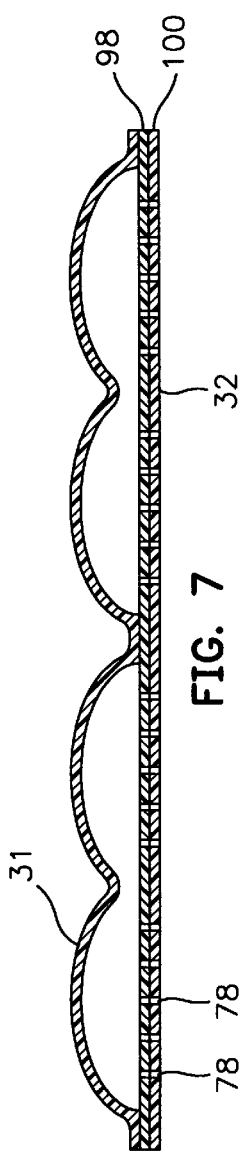

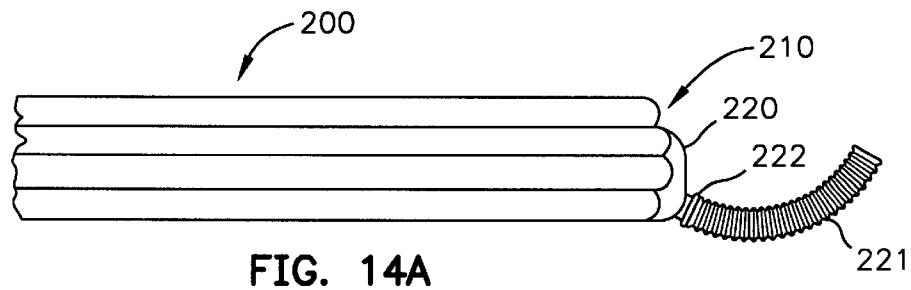
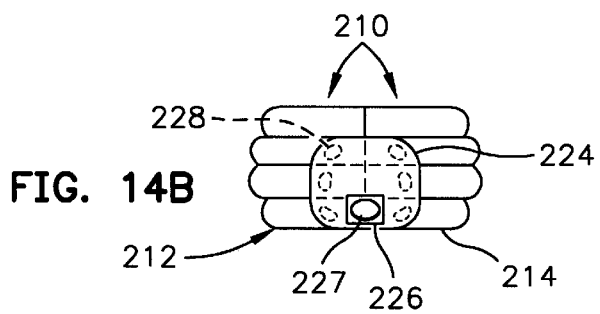
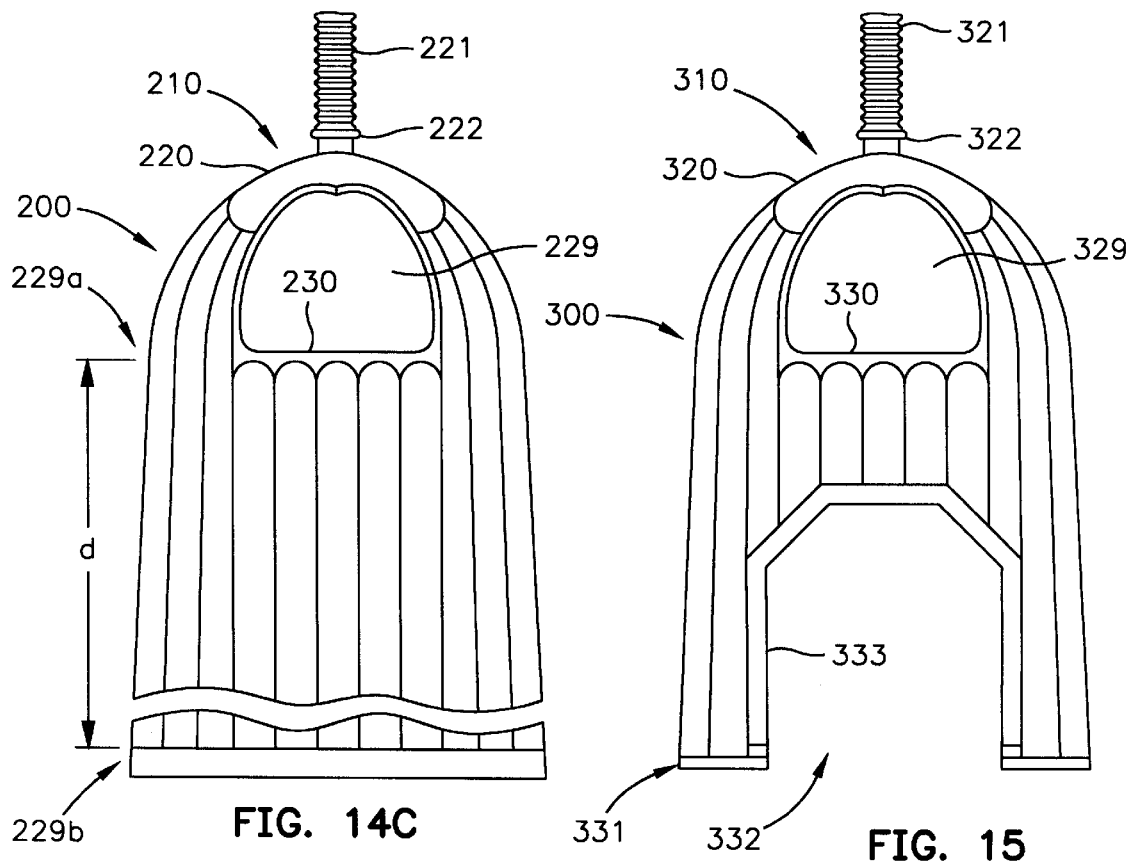

CONVECTIVE THERMAL BLANKET

This application is a continuation of application Ser. No. 08/667,480, filed Jun. 24, 1996, now U.S. Pat. No. 5,658,325, which is a continuation of application Ser. No. 08/380,264, filed Jan. 27, 1995, now abandoned, which is a continuation of application Ser. No. 08/285,921, filed Aug. 3, 1994, now abandoned, which is a continuation of application Ser. No. 08/063,214, filed May 18, 1993, now U.S. Pat. No. 5,350,417.

BACKGROUND OF THE INVENTION

1. Field of the Invention

The present invention relates to a thermal blanket and more particularly to a blanket which conditions the temperature of the trunk and head of a person by convection.

2. Related Prior Art

Every year thirty-five million patents in the United States and Europe will suffer from hypothermia if not properly treated. This condition has been treated using heated cotton blankets, warm water circulation blankets and mattresses, or infrared heating lamps. The material and labor costs for these products are significant. However, without this treatment the results can be discomfort, bleeding disorders, cardiac dysfunction and possibly death.

The most common method of warming a patient has employed a heated cotton blanket. The blanket, which is reusable, is preheated and then laid on the patient. After the blanket has dissipated its heat, it is used to cover another preheated blanket which is placed on the patient. This method of heating a patient requires a considerable amount of blanket preparation. Further, some people, such as diabetes patients, cannot tolerate the weight of a blanket on their feet. A more significant problem, however, is that the preheated blanket does not achieve a satisfactory result. Measurements have shown that the blanket does not heat the patient but simply acts as an insulation requiring the patient to produce the heat and warm himself.

A better mode of patient temperature control is provided by the circulating water blanket or mattress;. Warmed water is circulated through tubes inside the blanket or mattress, to warm the patient. This structure provides heat to the patient. However, the results from the circulating water blanket are still not optimum. The small surface area in contact with the blanket results in minimal heat transfer. Also, since the blanket contacts the patient, its weight or the patient's weight, applies heat and pressure to the patient's skin, frequently resulting in burns.

A significant advance in the prevention and treatment of hypothermia was made in my coauthored U.S. Pat. No. 4,572,188, entitled "AIRFLOW COVER FOR CONTROLLING BODY TEMPERATURE". Improvements to the airflow cover disclosed and claimed in the '188 patent are found in the following co-pending, commonly assigned U.S. patent applications:

Ser. No. 07/703,592, filed May 20, 1991, now U.S. Pat. No. 5,324,320; and

Ser. No. 07/887,233, filed May 19, 1992, now U.S. Pat. No. 5,300,102.

The patent and both of these patent applications are incorporated herein by reference. The latter incorporated U.S. patent application incorporates a foot drape into a convective thermal blanket. Commonly assigned U.S. Pat. No. 5,184,612, which is also incorporated by reference, describes a convective thermal blanket with an uninflatable, transparent upper body drape for covering the chest area and enabling viewing thereof. The airflow cover of the '188 patent and the thermal blanket of the incorporated U.S. applications and '612 patent comprise inflatable, self-erecting structures which cover a patient and exhaust warmed inflating air onto a covered patient. These products safely, and efficiently elevate and maintain patient body temperature. The fast and widespread acceptance of these products by the marketplace testifies to their effectiveness. Since 1988, over four million patients have been warmed by convective blankets manufactured according to the teachings of the '188 patent. These products are referred to as Bair Hugger® thermal blankets. Bair Hugger® is a trademark owned by Augustine Medical, Inc., the assignee of this patent application.

Since the introduction of Bair Hugger® products, a number of other inflatable, convective thermal blankets have been introduced into the marketplace. Such blankets operate in the same manner as the airflow cover described in the '188 patent; that is, they comprise an inflatable cover with multiple airflow paths and apertures which open through the bottom of the cover to exhaust warmed inflating air from the cover onto a patient. Hereinafter, these products are referred to as "Augustine-type" convective thermal blankets.

Some very important comparisons have been made between Augustine-type convective thermal blankets and prior art non-convective devices. See, for example, D. I. Sessler, M.D., et al., "Skin-Surface Warming: Heat Flux and Central Temperature", in ANESTHESIOLOGY, Vol. 73, p-218–224, 1990 and J. M. Hynson, M.D., et al, "Intraoperative Warming Therapies: A Comparison of Three Devices". Journal of Clinical Anesthesiology, Vol. 4, p-194–199. 1992.

One significant omission in the design and operation of prior art thermal blankets of the Augustine type is that they provide no way to control heat loss or gain through a patient's head. The head, like the core or trunk of a patient's body, is one of the areas of the greatest heat loss or gain. It would therefore be desirable to provide a single means and mode of treatment which would actively warm the head of the patient as well as the rest of the body. A cap for heating a patient's head is described in the '188 patent. However, this head heating device is separate from the airflow cover described in the patent and requires a separate hose attachment. It would be desirable to heat both the head and chest areas with a single convective thermal blanket of the Augustine type.

STATEMENT OF THE PRESENT INVENTION

One of the primary purposes of the present invention is to warm a patient's head with the same efficiency as the patient's body using an Augustine-type thermal blanket. In this regard, an object of the present invention is to employ a single convective thermal blanket with a single hose for warming both the core and the head of a patient. This has been accomplished by providing a convective thermal blanket of: the Augustine-type which has an inflatable covering including top and bottom layers of material which are adapted to cover at least a portion of a patient's chest and head areas. The inflatable covering has longitudinally spaced apart head and foot edges and laterally spaced apart side edges, the edges being substantially continuous with respect to one another so as to collectively provide the covering with a periphery.

A head portion of the inflatable covering has a recess which forms the head portion into a pair of laterally spaced apart flaps which are capable of receiving a patient's head therebetween. The recess also provides the head edge of the covering with a recess edge portion. Each flap is formed by a respective recess edge portion and a respective side edge portion. The top and bottom layers of the covering are sealed about the periphery so as to form a main plenum chamber which is in inflatable communication with a secondary plenum chamber in each flap. The inflatable covering has an opening which opens into the main plenum chamber for receiving a gaseous medium to inflate the main plenum chamber and the secondary plenum chambers. The bottom layer of the covering has a plurality of small apertures which open into the main plenum chamber and each secondary plenum chamber. A gaseous medium, such as heated air, can then be introduced into the main plenum chamber through its inlet opening. This heated air fills the main plenum chamber as well as the secondary plenum chambers in the flaps so as to provide an inflating pressure therein. The heated air is then discharged through the plurality of small apertures in the bottom layer of the main plenum chamber over the patient's chest and the bottom layer of the secondary plenum chambers over the patient's head. With this arrangement, all of the benefits of the aforementioned Augustine-type thermal blanket are obtained for heating a patient's head as well as the rest of his body. It should be understood that the invention could also be used for cooling a patient's body. The invention has other unique features which will be fully described in the following description of the preferred embodiments.

An object of the present invention is to overcome the aforementioned problems associated with the prior art devices or treating hypothermia.

Another object is to extend the benefits of the Augustine-type thermal blanket to heating a patient's head.

A further object is to more efficiently condition the temperature of a patient's body including his head.

Still another object is to render postoperative hypothermia treatment which will minimize recovery room time.

Still a further object is to provide a disposable thermal blanket which heats the head and core of a patient's body.

Yet another object is to provide a low cost, lightweight, disposable and highly efficient thermal blanket for heating the head and core of a patient's body to prevent hypothermia.

These and other important objectives and advantages will become evident when the detailed description of the invention is read with reference to the below summarized drawings.

BRIEF DESCRIPTION OF THE DRAWINGS

FIG. 1 is a side view of the convective thermal blanket of the present invention in use.

FIG. 2 is a head end view of the convective thermal blanket covering a patient's head.

FIG. 4 is a cross-sectional view taken along plane 4—4 of FIG. 3.

FIG. 5 is a cross-sectional view taken along plane 5—5 of FIG. 3.

FIG. 6 is a cross-sectional view taken along plane 6—6 of FIG. 3.

FIG. 7 is a cross-sectional view taken along plane 7—7 of FIG. 3.

FIG. 13 is an enlarged cross-sectional view through a pair of apertures in the bottom layer of the convective thermal blanket.

FIGS. 14A–14C are partial side elevational, head end elevational, and top plan views of a third embodiment of the invention.

FIG. 15 is a top plan view of a variation of the third embodiment illustrated in FIGS. 14A–14C.

DETAILED DESCRIPTION OF THE PREFERRED EMBODIMENTS

Figure 3:
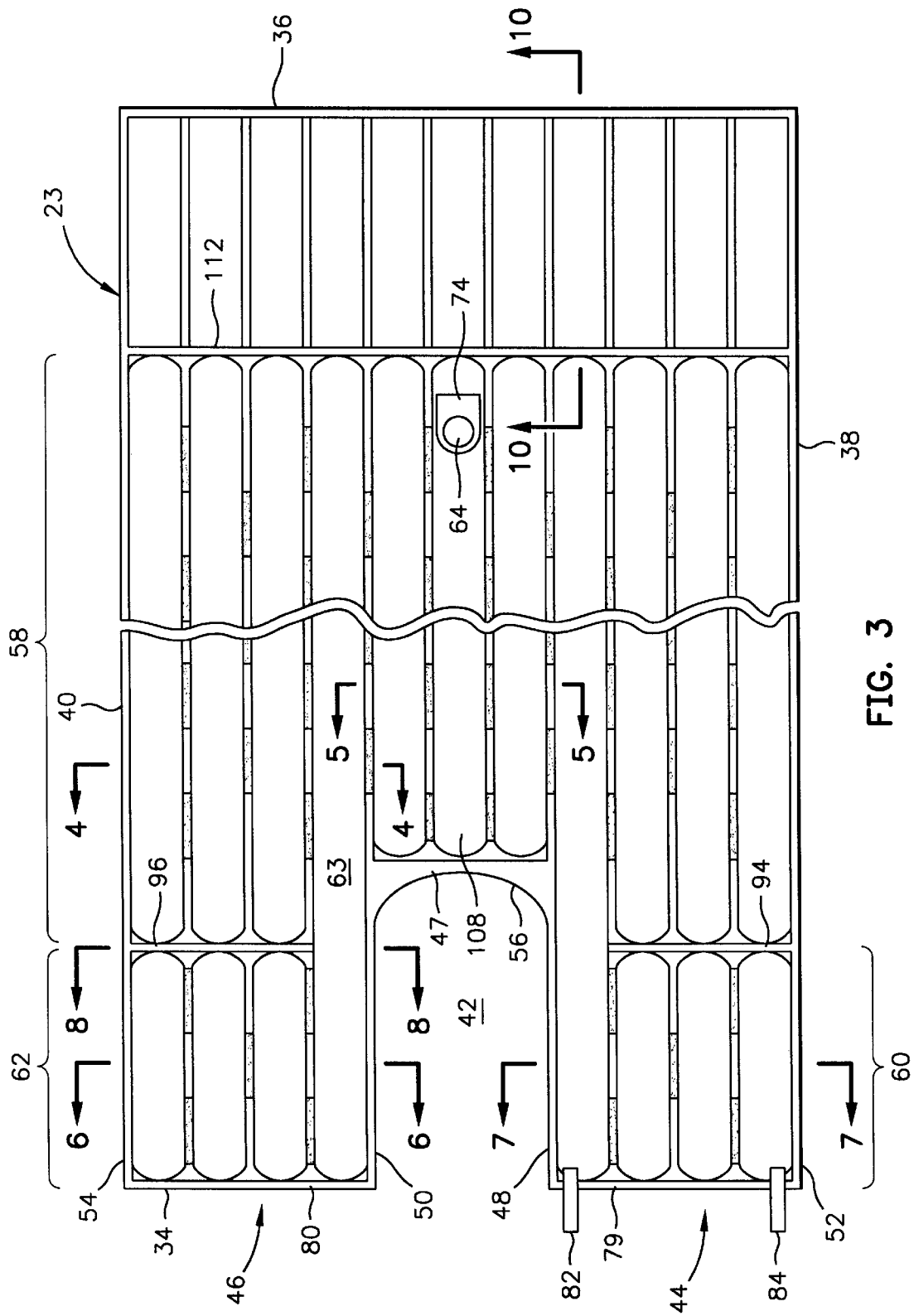
FIG. 3 is a top planar view of the convective thermal blanket.
Figure 8:
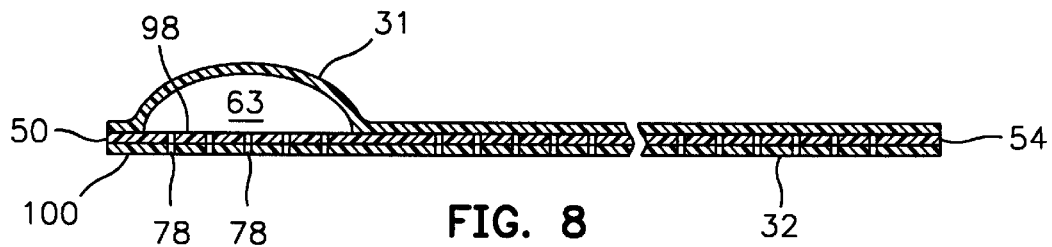
FIG. 8 is a cross-sectional view taken along plane 8—8 of FIG. 3.
Figure 10:
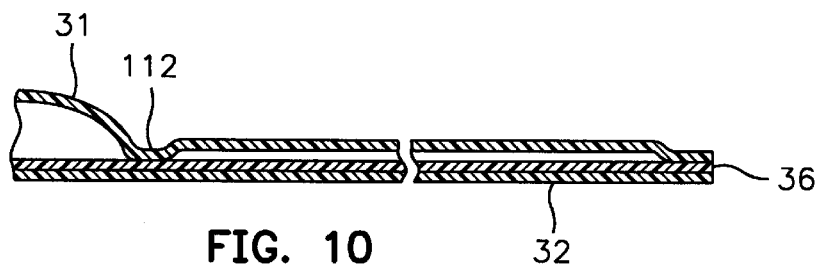
FIG. 10 is a cross-sectional view taken along plane 10—10 of FIG. 3.
Figure 9:
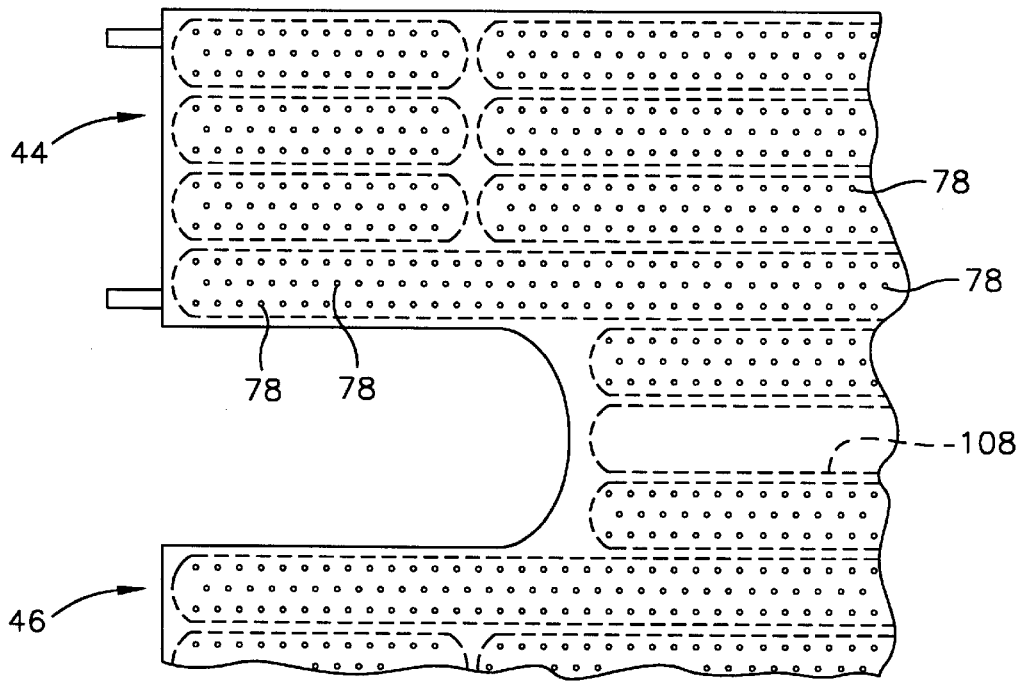
FIG. 9 is a bottom view of the convective thermal blanket.

Referring now to the drawings wherein like reference numerals designate like or similar parts throughout the several views there is illustrated in FIGS. 1–3 a convective thermal blanket which is indicated generally by 20. The convective thermal blanket 20 is a preferred embodiment and includes an inflatable covering 22 and an uninflatable foot drape 23. The embodiment of FIG. 1 provides coverage of the entire body of the patient including the patient's chest, leg, and head portions indicated, respectively, by reference numerals 28, 29, and 30. The preferred embodiment also includes the uninflatable foot drape 23 which extends over and covers up the patient's feet, trapping warmed air expelled through the inflatable covering 22 for warming the feet. Other embodiments of the invention may include only an inflatable covering which covers a patient's chest, legs, and head or a patient's chest, arms, and head. The inflatable covers of these other embodiments (which may or may not include uninflatable drapes) may also be referred to as "convective thermal blankets."

As illustrated in FIGS. 4–10 and 13, the inflatable covering 22 of the convective thermal blanket illustrated in FIG. 1 has top and bottom layers of material 31 and 32. As illustrated in the figures described below, these layers are sized to cover the chest, leg, and head of a patient. However, as stated above, the inventor contemplates that these layers may be sized to cover at least a patient's chest and head areas.

With reference to FIG. 3, the inflatable covering 22 has longitudinally spaced apart head and foot edges 34 and 36 and laterally spaced apart side edges 38 and 40. These edges are continuous with respect to one another so as to collectively provide the convective thermal blanket 20 with a periphery. In alternate embodiments which would not include the uninflatable foot drape 23, the foot edge of the convective thermal blanket would coincide with a foot edge of the inflatable covering, whatever its size.

The inflatable covering 22 has a head portion 24 with a recess 42. As illustrated in FIGS. 2 and 3, the recess 42 forms the head portion 24 into a pair of laterally spaced apart flaps 44 and 46 which are capable of receiving a person's head therebetween. The recess 42 provides the head edge 34 of the covering with a recess edge portion 47. Each flap 44 and 46 is formed by a respective portion 48 and 50 of the recess edge portion 47 and a respective side edge portion 52 and 54. As shown in FIG. 3, the recess edge portion 47, is generally U-shaped with the spaced-apart sides of the U being the aforementioned recess edge portions 48 and 50 of the flaps 44 and 46. The recess edge portion 47 is completed by a bottom edge portion 56 of the U portion which joins its side edge portions 48 and 50. As shown in FIG. 1, the bottom edge portion 56 is adapted to be positioned on or over a patient's chest when the patient is covered by the inflatable covering 22.

The top and bottom layers 31 and 32 of the inflatable covering 22 are sealed together along the periphery so as to form a main plenum chamber and a pair of secondary plenum chambers. Refer to FIGS. 1 and 3 wherein the main plenum chamber is indicated by reference numeral 58, while the pair of secondary plenum chambers are indicated by reference numerals 60 and 62. The main plenum chamber 58 in the preferred embodiment of FIG. 1 corresponds essentially to the lower portion of the inflatable covering 22 that covers the chest and leg areas 28 and 29 of the patient, while the secondary plenum chambers 60 and 62 are respective portions of the inflatable covering found in the flaps 44 and 46. As illustrated in FIG. 1 and explained below, the secondary plenum chambers 60 and 62 are adapted to enclose the head area 30 of the patient.

The main plenum chamber 58 is in communication with each of the secondary plenum chambers 60 and 62 so that an inflating medium introduced into any one of the plenum chambers will inflate them all. For the preferred embodiment, the inflatable communication between the main plenum chamber 58 and the secondary plenum chamber 62 can be understood with reference to FIGS. 3 and 8. In this regard, communication is through an elongate inflatable tube 63 which conducts an inflating medium in either direction between the plenum chambers 58 and 62 by means described in greater detail below. The inflatable communication of the main plenum chamber 58 with the other secondary plenum chamber 60 is identical with that illustrated in FIGS. 3 and 8.

As shown in FIGS. 1 and 3, the inflatable covering 22 is provided with an opening 64 which opens into the main plenum chamber 58 for receiving a gaseous medium to pressurize and inflate the covering. The gaseous medium, which may be heated air, is provided by a unit 66 which has a compressor 68 and a heater 70, the compressor and heater being controlled by a controller 72. The opening 64, which may extend through the top layer 31, may be provided with a cuff 74 which is adapted to receive a hose 76 from the unit 66. With this arrangement pressurized heated air can be conducted into the main and secondary plenum chambers 58, 60 and 62 for inflating the inflatable covering 22.

As shown in FIGS. 4 through 8, the bottom layer 32 of the inflatable covering 22 has a plurality of small apertures 78 which open into the main plenum chamber 58 and the secondary plenum chambers 60 and 62. These apertures enable the heated air from the unit 66 to be discharged over the patient's body, especially in the chest, leg, and head areas 28, 29, and 30, when the plenum chambers 58, 60 and 62 are inflated. It should be noted that the density or size of the apertures 78 can be varied in order to increase or decrease the concentration of heated air on particular portions of the patient's body. For instance, if it is desired to have more heat applied to the patient in the chest area, the density (number) and size of the apertures 78 in this area can be increased. Since the major heat loss of a patient is in the chest and head areas, it may be desirable to have an increased density of apertures in these areas.

As shown in FIGS. 1–3, the flaps 44 and 46 are sized to extend far enough to cover the top of a patient's head when the patient is covered with the convective thermal blanket 20. As best seen in FIG. 3, the head edge 34 of the inflatable covering 22 has a pair of laterally extending head edge portions 79 and 80 which are laterally spaced apart by the recess 42. Each lateral head edge portion 79 and 80 forms a distal end edge of a respective flap 44 and 46. As shown in FIGS. 1–3, provision is made for connecting the flaps 44 and 46 together so that they cover the sides and top of the patient's head, but leave an opening to expose the patient's face. This may be accomplished by sticky-sided tabs 82 and 84 which are connected to one of the flaps, such as flap 44. The sticky sides of these tabs 82 and 84 extend beyond the lateral edge 79 of the flap 44 so that they can attach to the other flap 46 to hold the flaps 44 and 46 in a position surrounding the top of a patient's head, as illustrated in FIGS. 1 and 2. It should be understood that this is an exemplary embodiment for attaching the flaps above the patient's head, and other provisions can accomplish the same purpose. For instance, a single large sticky tab, one or more squeeze-type clips, snaps, ties, or hook and eye fasteners could be employed to secure overlapping distal ends 79 and 80 of the flaps above the patient's head.

Figure 11:
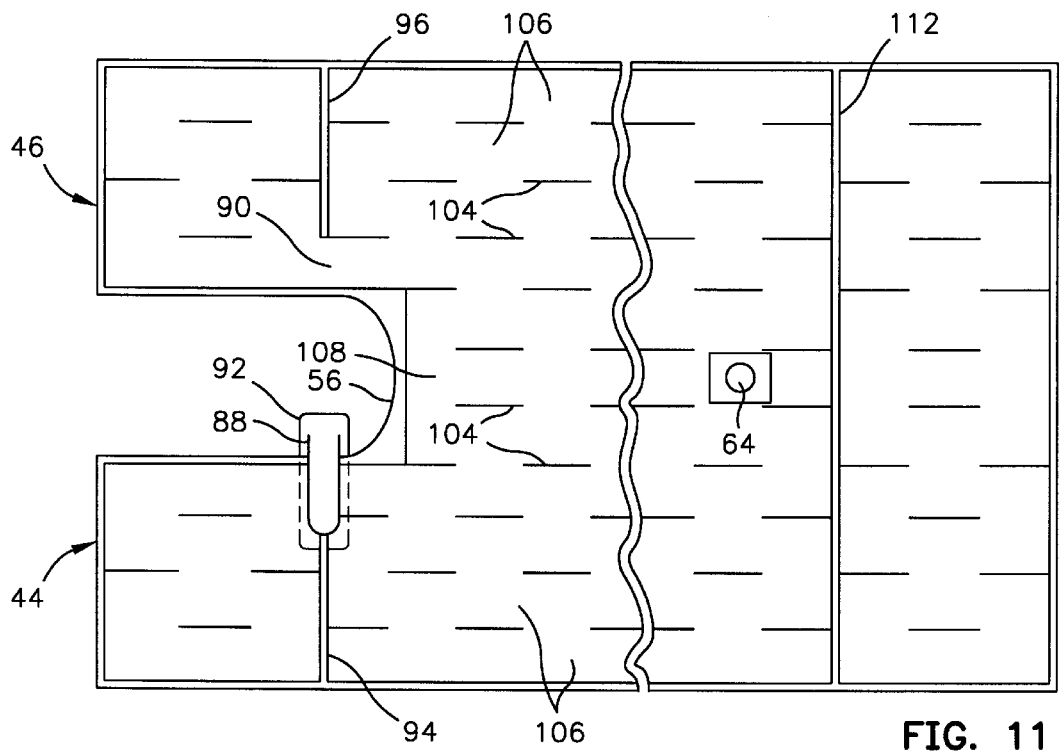
FIG. 11 is a schematic illustration of one embodiment of the invention.
Figure 12:
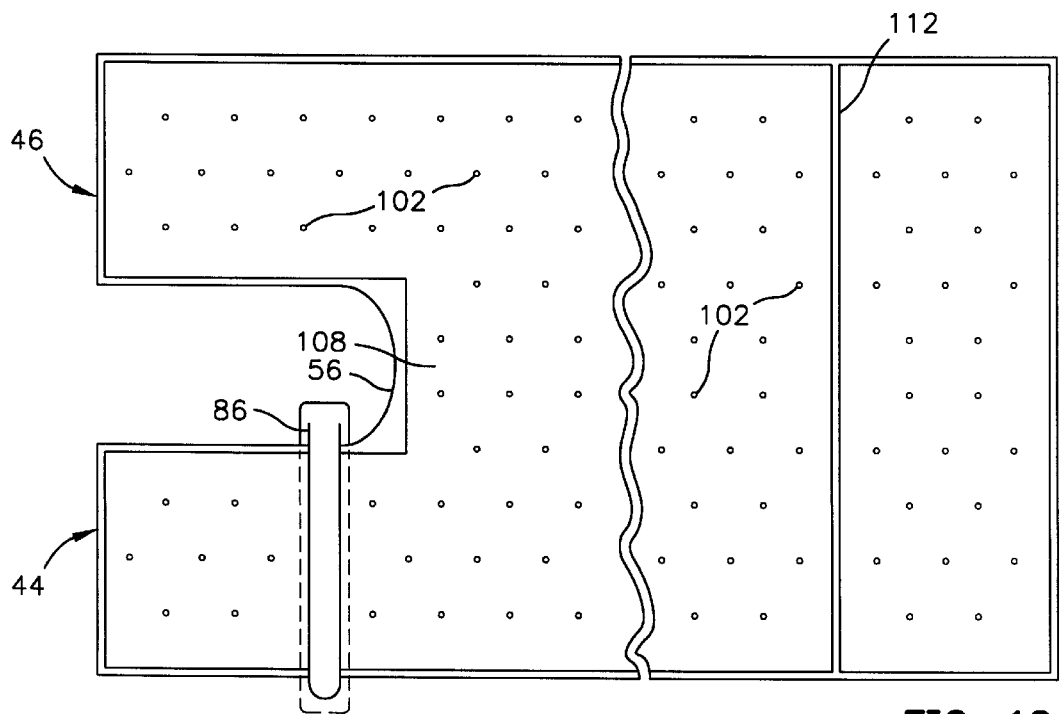
FIG. 12 is a schematic illustration of another embodiment of the present invention.

In some instances, it may be desirable to seal off the secondary plenum chambers 60 and 62 so that no heat or cooling is applied to the head portion of a patient. As shown in FIGS. 11 and 12, provision may be made for selectively sealing the plenum chambers 60 and 62 from the main plenum chamber 58. As shown in FIG. 11, this may be accomplished by elongate clips, one of which (indicated by reference number 92) is shown sealing off the flap 44. In the preferred embodiment, seals 94 and 96 extend medially from respective side edges 52 and 54 of the flaps to a distance short of the flaps' inner recess edge portions 48 and 50 so that restricted openings 88 and 90 are formed adjacent the bottom recess edge portion 56. With this arrangement, the clips 86 can be inserted from inside the flaps 44 and 46 a short distance to seal off the secondary plenum chambers 60 and 62 of the flaps 44 and 46 from the main plenum chamber 58. Alternatively, larger clips 86 could be employed, as shown in FIG. 12, where the flaps 44 and 16 are not partially sealed from the main plenum chamber 58 by the seals 94 and 96 of FIG. 11. In this instance, the clips 86 extend laterally entirely across the flaps from their inner edges 48 and 50 to their outer edges 52 and 54 adjacent the bottom edge portion 56 of the recess edge.

As shown in FIGS. 4–8, the bottom layer 32, which provides the bottom of the main and secondary plenum chambers 58, 60 and 62, may comprise a laminate of upper and lower thin sheets of material 98 and 100. The upper sheet 98 is preferably a thermoplastic material sheet and the lower sheet 100 is preferably a soft tissue-like paper sheet. The thickness of the thermoplastic sheet 98 may be approximately ¾ of a mil. and the thickness of the paper sheet 100 may be approximately 1 mil. The thermoplastic sheet 98 is bonded to the paper sheet 100 by a heat process or gluing and is commercially available in large rolls. The top layer 31 of the covering may also be a sheet of thermoplastic material with a thickness of approximately ¾ of a mil.

As shown in FIGS. 3, 4 through 8, 11 and 12, the top and bottom layers 31 and 32 may be sealed to one another at a plurality of locations so as to provide a plurality of passageways therein. As shown in FIG. 12, a plurality of random or staggered spot seals 102 may be employed for providing these passageways. In the preferred embodiment shown in FIGS. 3, 4–8 and 11, a plurality of elongated seals 104 are spaced along parallel lines to provide a plurality of longitudinal tubes 106. These longitudinal tubes 106, which are in communication with one another, vent laterally outwardly, one to the other, from the inlet opening 64. The seals 102 and 104 may be formed by sealing the top plastic layer 31 to the bottom plastic layer 98 at the illustrated locations. The sealing process may include applying heating elements (not shown) against the paper layer 100 which causes heat to transfer across the paper layer and fuse the plastic sheets together. In the preferred embodiment, the elongated seals 104 are spaced along a respective line with a seal to space ratio in a range of between one/one to twelve/one. This provides a more uniform distribution of heated air over the patient's body.

As shown in FIGS. 3 and 11, a preferred embodiment of the inflatable covering 22 has a centrally located longitudinal tube 108 with longitudinal tubes 106 on each side thereof. In the preferred embodiment, the opening 64 opens into this central passageway 108; however, the opening may be placed at any location deemed necessary to proper blanket operation. Further, in the preferred embodiment, no openings 78 are placed in the bottom layer 26 of the central tube 108. With this arrangement, the slightly pressurized heated air can be first channeled laterally to the adjacent passageways 104, after which it is discharged from the passageways 104 more uniformly over the patient's body.

In the preferred embodiment, the apertures 78 in the bottom layer 26 have ragged outlet edges 110 (see FIG. 13) which diffuse the heated air across the patient's body. When the heated air exits these apertures 78, the ragged edges 110 interrupt the flow so that it is not concentrated on the patient's body. If the apertures 78 had clean cut edges, the heated air would be directed in pencil-like streams. It is more desirable that the stream be broken up by the ragged edges 110 so that the heated air is distributed more evenly over the patient's body. These ragged edges are made by piercing the bottom layer 32 which causes the fibers of the lower layer 100 to project outwardly in a random fashion.

In the embodiment of the thermal blanket shown in FIGS. 1 and 3, the inflatable covering 22 extends over the leg area 29 to provide heat to the legs and includes an uninflatable foot drape portion 23. As shown in FIGS. 1, 3, 11 and 12, a transverse seal 112 may be located between the bottom edge 36 of the covering and the opening 64 in the main plenum chamber 58. This seal may extend from the side edge 38 to the side edge 40 so as to completely seal off the foot drape portion 23 of the thermal blanket from the main plenum chamber 58. With this arrangement, the foot drape portion 23 is uninflatable and will not discharge heated air over the patient's feet. As discussed hereinabove, it is more important to heat the core or chest area 28 and the head area 30 of the patient rather than the leg portions. It should be noted that a portion of the warm air distributed to the chest area 28 of the covering will vent underneath the bottom layer 26 into the space beneath the foot drape 23.

The thermal blanket 20 provides an inflatable covering 22 for the patient which will optimize heating those portions of the body which are most critical for overcoming hypothermia. In addition to the chest area, the invention now provides for heating the head area of the patient so as to more quickly achieve the desired normothermia condition. The thermal blanket with the inflatable covering 22 placed over the patient as illustrated in FIG. 1, is connected by the hose 76 to the unit 66. The unit 66 is activated to produce heated air into the 80 main plenum chamber 58 and the secondary plenum chambers 60 and 62 of the flaps 44 and 46. The flaps can be easily wrapped around the top of the patient's head by the tabs 82 and 84 so that the head is heated on both sides as well its top. An increase in airflow or temperature can be controlled by the controller 72 as desired. The foot drape 23 provides passive heating for the foot area. The particulars of this invention also enable the product to be easily manufactured. Heating elements are simply applied against the paper layer 98 according to the patterns of FIGS. 11 or 12. This causes the thermoplastic layers 24 and 98 to bond. The heating elements do not stick to the thermoplastic layers because the heat is applied through the paper layer 100.

Refer now to FIGS. 14A–14C for an understanding of another embodiment of a convective thermal blanket according to the invention. In these figures, the convective thermal blanket is illustrated as an inflatable covering, with the understanding that uninflatable portions may be added at various locations in the illustrated covering as required by any particular application. These figures illustrate how the convective thermal blanket with a head portion for surrounding and convectively warming the head of a patient may be further varied from the embodiments discussed above by provision of an air inlet means at the head end of the covering. In this regard, the convective thermal blanket includes an inflatable covering 200 with an inflatable head end portion 210. The covering 200 and head end portion may be constructed as described above for the embodiments shown in FIGS. 1–13, with the head end flaps sealed together at their ends. In FIGS. 14A, 14B, and 14C, the blanket is shown in elevational and plan views, with the understanding that, when inflated, the inflatable covering erects into a structure whose inner surface contains small apertures for expelling an inflating medium from the inflatable covering onto a patient. In these figures, an air inlet assembly 220 is illustrated for inflating the covering 200 by provision of heated, pressurized air through a hose 221 having an end portion 222. The air inlet assembly 220 includes a shaped sheet 224 of relatively thick (1.0 to 1.5 mil), flexible plastic material which can be attached by two-faced adhesive tape or heat bonded around its periphery to the plastic sheet forming the upper layer of the inflatable covering 200 at the head end. A cardboard cuff 226 is fixed to the sheet 224 over an inlet aperture 227 which receives the end 222 of the hose 221. Prior to attachment or bonding, holes or ports, one of which is indicated by 228, are opened into the upper sheet of the inflatable covering 200. This provides an inflatable communication between the hose end 222 and the interior of the inflatable covering 200 so that the covering 200 may be inflated in its entirety by introduction of warmed, pressurized air at its head end 210 through the air inlet assembly. FIGS. 14A–14C illustrate in various views the form of an inflatable covering having a structure comprising mutually communicating inflatable tubes. The inventor contemplates that the air inlet assembly 220 is applicable as well to inflatable coverings having non-tubular structures. Further, the inventor contemplates that the inflatable covering 200 may have a longitudinal extent defined by a distance d extending essentially from the bottom end of the opening 229 provided for the face of a patient. In FIG. 14C, the distance d extends from a lower edge 229a in the opening 229 to an end seal 229b coextensive with the lower end of the inflatable covering 200. This distance d may take on values of sufficient magnitude to extend at least to the lower chest or waist of a patient, to a patient's legs, or over a patient's feet.

In FIG. 15, an alternate embodiment of the convective thermal blanket of FIGS. 14A–14C is illustrated. As shown, this embodiment includes an inflatable covering 300 with a head end 310 for enclosing and convectively warming the head of a patient. This embodiment includes an air inlet mechanism 320 conforming essentially with that illustrated in FIGS. 14A–14C which is attached to the end 332 of an air hose 331. This convective thermal blanket includes a face opening 329 with a lower edge 330. This distance d between lower edge 330 and the end seal 331 is limited to extend substantially to the waist of a patient. The embodiment of FIG. 15 includes a cutout area 332 having a substantially continuous seal forming a perimeter 333 which has an adhesive undersurface for sticking to the skin of a patient. The adhesive undersurface of the perimeter 333 forms a seal between the inflatable covering 330 and the body of a patient to confine warmed air exhausted through the small apertures (not shown) in the underside of the inflatable covering and to prevent the air from flowing across a surface of the patient located within the cutout area 332. The embodiment of the convective thermal blanket illustrated in FIG. 15 is intended for use, for example, during surgery performed in the chest or abdomen area of a patient when it is necessary to control hypothermia.

Many modifications and variations of my invention will be evident to those skilled in the art. It is to be understood that such variations may deviate from specific teachings of this description without departing from the essence of the invention, which is expressed in the following claims.

I claim:

1. A convective thermal blanket comprising:

a covering having top and bottom layers of material;

the covering having longitudinally spaced apart head and foot edges, laterally spaced apart side edges and a periphery;

a head portion at the head edge of the covering having a recess which forms the head portion into a pair of laterally spaced-apart flaps for receiving a person's head therebetween, the recess providing the head edge of the covering with a recess edge portion;

the top and bottom layer of the covering being sealed about the periphery so as to form a main chamber and a pair of secondary chambers which are in communication with respect to one another;

an inlet assembly in the head portion for receiving a flow of air to pressurize and inflate the covering; and the bottom layer of the covering having a plurality of apertures for discharging the air.

2. A convective thermal blanket, as claimed in claim 1, including:

a unit for producing a pressurized inflating flow of air; and a hose connecting the unit to the covering at the inlet assembly for introducing the flow of air into the main and secondary chambers.

3. A convective thermal blanket, as claimed in claim 1, including:

the bottom layer of the covering including a laminate of upper and lower thin sheets of material, the upper sheet of material being a thermoplastic sheet and the lower sheet of material being a soft tissue-like sheet;

the top layer of the covering including a thin sheet of thermoplastic material; and the top and bottom layers of the covering being sealed between the thermoplastic sheets of material.

4. A convective thermal blanket, as claimed in claim 3, including:

the top and bottom layers of the covering being sealed together at a plurality of locations within the periphery so as to form a plurality of passageways.

5. A convective thermal blanket, as claimed in claim 4, including:

the plurality of locations being aligned along a plurality of laterally spaced, longitudinally extending parallel paths so as to form a plurality of intercommunicating longitudinal passageways within the main and secondary chambers.

6. A convective thermal blanket, as claimed in claim 5, including:

the covering having a centrally located longitudinal passageway with a plurality of longitudinal passageways located on each side thereof.

7. A convective thermal blanket, as claimed in claim 1, including:

the covering having at least one extended portion; and the covering having a seal located so as to seal off the at least one extended portion of the covering from the main chamber, the at least one extended portion being adapted to serve as an uninflated drape.

8. A convective thermal control blanket comprising:

an inflatable covering including top and bottom layers of material;

the top and bottom layers being sealed together at their peripheries;

a first end of the covering having a recess for receiving a person's head, the recess forming a top portion of the covering into a pair of inflatable flaps, each flap being adapted to extend along a respective side of the head, and leaving an inflatable lower portion of the covering which is adapted to cover at least the person's chest area;

the covering having an inlet assembly in the top portion for admitting a flow of air to inflate the lower portion and the flaps; and the bottom layer of the covering having a plurality of apertures, which open into the lower portion and the flaps, for discharging the air over the chest and head areas when the covering is inflated.

9. A convective thermal control blanket as claimed in claim 8, including:

a unit for providing a flow of pressurized inflating air; and hose connecting the unit to the covering at the inlet assembly for introducing the flow of air into the lower portion and the flaps.

10. A convective thermal control blanket, as claimed in claim 8, including:

the covering having an extended uninflatable portion.

11. A convective thermal control blanket, as claimed in claim 8, comprising:

the flaps being adapted to extend along and across the top of the patient's head; and the inlet assembly including a sheet of material attaching the flaps together.

12. A convective thermal control blanket, as claimed in claim 11, including:

said bottom layer of the covering being a laminate of upper and lower thin sheets of material, the upper sheet of material being a thermoplastic sheet and the lower sheet being a soft tissue-like sheet;

said top layer of the covering being a thin sheet of thermoplastic material; and the seal between the top and bottom layers of the covering acting between the thermoplastic sheets of material.

13. A convective thermal control blanket as claimed in claim 12, including:

the top and bottom layers of the covering being sealed together at a plurality of locations within the lower portion and flaps so as to form a plurality of airflow passageways therein.

14. A convective thermal control blanket, comprising:

an inflatable covering including top and bottom layers;

the top and bottom layers being sealed together at their peripheries and at a plurality of locations within their peripheries;

the bottom layer of the covering having a plurality of apertures for exhausting the inflating medium onto a person;

the inflatable covering including a head and a foot end and, at the head end, an extension for receiving and surrounding the head of a person within a space defined by a portion of the bottom layer; and an inlet assembly in the extension for admitting a flow of air to inflate the covering.

15. The convective thermal control blanket of claim 14, further including a chest opening near the foot end for exposing the chest of a person.

16. The convective thermal control blanket of claim 15, wherein the chest opening includes a periphery in the inflatable covering and an adhesive means on the periphery for attaching to the patient.

17. The convective thermal control blanket of claim 14, wherein the inlet assembly includes a sheet of flexible plastic material on the top layer at the head end, an inlet opening, a cuff means attached to the plastic sheet over the opening for receiving an inflating hose end, and one or more openings in the top layer of the inflatable covering underneath the plastic sheet.

* * * * *